United States Patent
Hong et al.

(10) Patent No.: US 9,415,081 B2
(45) Date of Patent: *Aug. 16, 2016

(54) COMPOSITION FOR PREVENTING OR TREATING AIDS CONTAINING PLANT STEM CELL LINE DERIVED FROM CAMBIUM OF PANAX GINSENG INCLUDING WILD GINSENG OR GINSENG AS ACTIVE INGREDIENT

(71) Applicant: UNHWA CORPORATION, Jeonju, Jeollabuk-do (KR)

(72) Inventors: Sun Mi Hong, Jeonju-si (KR); Eun Kyong Lee, Iksan (KR); Young Woo Jin, Jeonju (KR)

(73) Assignees: UNHWA CORPORATION, Jeonju-Si, Jeollabuk-Do (KR); Young Woo Jin, Jeonju-Si, Jeollabuk-Do (KR); Eun Kyounng Lee, Jeonju-Si, Jeollabuk-Do (KR)

( * ) Notice: Subject to any disclaimer, the term of this patent is extended or adjusted under 35 U.S.C. 154(b) by 191 days.

This patent is subject to a terminal disclaimer.

(21) Appl. No.: 13/803,963

(22) Filed: Mar. 14, 2013

(65) Prior Publication Data

US 2014/0099285 A1    Apr. 10, 2014

Related U.S. Application Data

(63) Continuation of application No. 13/121,930, filed as application No. PCT/KR2009/005618 on Sep. 30, 2009, now abandoned.

(30) Foreign Application Priority Data

Sep. 30, 2008 (KR) .................. 10-2008-0095877

(51) Int. Cl.
   *C12N 5/04*    (2006.01)
   *A61K 36/258*  (2006.01)
   *A01H 4/00*    (2006.01)
   *A23L 1/30*    (2006.01)

(52) U.S. Cl.
   CPC .............. *A61K 36/258* (2013.01); *A01H 4/005* (2013.01); *A23L 1/30* (2013.01); *A23L 1/3002* (2013.01); *C12N 5/04* (2013.01); *A23V 2002/00* (2013.01)

(58) Field of Classification Search
   None
   See application file for complete search history.

(56) References Cited

U.S. PATENT DOCUMENTS 7,413,756 B2 *  8/2008  Shan et al. .................... 424/728
8,247,230 B2    8/2012  Jang et al.
2008/0318876 A1 * 12/2008  Li et al. ........................ 514/26
2010/0255585 A1  10/2010  Yu et al.
2010/0272692 A1  10/2010  Park et al.
2011/0097310 A1   4/2011  Jang et al.
2011/0117039 A1   5/2011  Lee et al.
2011/0217273 A1   9/2011  Hong et al.
2011/0229443 A1   9/2011  Jin et al.
2012/0039918 A1   2/2012  Lim et al.
2012/0189660 A1   7/2012  Jin et al.

FOREIGN PATENT DOCUMENTS

WO    WO 2006026924 A1 *  3/2006

OTHER PUBLICATIONS

Choi, Kwang-tae; "Botanical characteristics, pharmacological effects and medicinal components of Korean Panax ginseng C A Meyer" Acta Pharmacologica Sinica, 29, 1109-1118, 2008.*
Gui, Y; et al; "Somatic embryogenesis and plant regeneration in Acanthopanax senticosus" Plant Cell Reports, 9, 514-516, 1991.*
Sung, Heungsup, et al.; "Korean Red Ginseng Slows Depletion of CD4 T Cells in Human Immunodeficiency Virus Type 1-Infected Patients," Clinical and Diagnostic Laboratory Immunology, 2005, vol. 12, pp. 497-501.
Cho, Young Keol, et al.; "Long-term intake of Korean red ginseng in HIV-1-infected patients; Decelopment of Resistance Mutation to Zidovudine is Delayed," International Immunopharmacology, 2001, vol. 1, pp. 1295-1305.
Wareing, PF, et al.; "The Role of Endogenous Hormones in Cambial Activity and Xylem Differentiation, The Formation of Wood in Forest Trees," Academic Press, 1964, pp. 323-344, New York.
Cho, Y, et al.; "High Frequency of Grossly Deleted nef Genes in HIV-1 Infected Long-Term Slow Progressors Treated with Korean Red Ginseng," Current HIV Research, 2006, pp. 447-457, vol. 4.
Digby, J, et al.; "The Effects of Growth Hormones on Cell Division and Expansion in Liquid Suspension Cultures of Acer pseudoplantus," Journal of Experimental Botany, 1966, vol. 17, pp. 718-725.

* cited by examiner

*Primary Examiner* — Renee Claytor
*Assistant Examiner* — David Berke-Schlessel
(74) *Attorney, Agent, or Firm* — Tristan A. Fuierer; Moore & Van Allen, PLLC (57) ABSTRACT

The present invention relates to a composition for preventing or treating acquired immunodeficiency syndrome (AIDS), comprising one or more of the following: a homogenous cell line, and a lysate, an extract and a culture thereof as an active ingredient. The homogenous cell line, the lysate, the extract and the culture thereof, which are derived from a natural product, minimize adverse side effects of prior therapeutic agents and safe for the human body. Further, they effectively increase the count of T cells such as CD4+ T cells and decrease the number of HIVs, thereby preventing opportunistic infection, dysneuria, and neoplaia caused by immune incompetence, and ultimately the risk of death. Therefore, they are useful in preventing and treating AIDS, and relieving symptoms of AIDS.

11 Claims, 3 Drawing Sheets

COMPOSITION FOR PREVENTING OR TREATING AIDS CONTAINING PLANT STEM CELL LINE DERIVED FROM CAMBIUM OF PANAX GINSENG INCLUDING WILD GINSENG OR GINSENG AS ACTIVE INGREDIENT

CROSS REFERENCE TO RELATED APPLICATIONS

This application is a continuation application of and claims the priority of U.S. patent application Ser. No. 13/121,930 filed on May 20, 2011, entitled "COMPOSITION FOR PREVENTING OR TREATING AIDS CONTAINING PLANT STEM CELL LINE DERIVED FROM CAMBIUM OF *PANAX GINSENG* INCLUDING WILD GINSENG OR GINSENG AS ACTIVE INGREDIENT" in the name of Sun Mi HONG, et al., which claims priority of International Patent Application No. PCT/KR2009/005618 filed on 30 Sep. 2009, which claims priority of Korean Patent Application No. 10-2008-0095877 filed on 30 Sep. 2008, all of which are hereby incorporated by reference herein in their entireties.

FIELD OF THE INVENTION

The present invention relates to a composition for preventing or treating acquired immunodeficiency syndrome (AIDS), comprising one or more of the following: a cell line derived from the cambium of *Panax ginseng* including wild ginseng and ginseng, and a lysate, an extract and a culture thereof, as an active ingredient.

BACKGROUND OF THE INVENTION

Since an AIDS (acquired immunodeficiency syndrome) patient was first found in 1982, in Los Angeles, USA, the number of patients has increased worldwide. In Korea, AIDS patients have steadily increased from the discovery of an American AIDS patient in 1985, requiring the development of new therapeutic agents.

Human immunodeficiency virus (HIV) is an enveloped virus that attacks mainly human lymphocytes, and belongs to a member of the retrovirus family as it converts its viral RNA genome to DNA by reverse transcription and integrates the resulting DNA into the cellular DNA of a host cell. HIV has RNA as its genetic information and reverse transcriptase within the viral core, which are surrounded by viral capsid proteins. This, in turn, surrounded by a protective lipid membrane comprising glycoproteins, gp120 and gp41, and gp120 is known to play a critical role in recognizing T-cells to invade thereinto.

HIV targets for CD4+ T cells, as CD4 cell membrane protein functions as a cell receptor for HIV-1 virus. The cell entry of HIV depends on gp120 which binds to intracellular CD4 receptor molecules, and HIV infection causes depletion of CD4+ T cells, thereby leading to immunological incompetence, opportunistic infection, dysneuria, neoplasia, and ultimately death.

Rapid increases in HIV-infected persons and AIDS patients have promoted the development of novel therapeutic agents in various countries, e.g., United States, France, Canada, Japan, and others. Until now, several anti-HIV agents, including 2,3-azidothymidine (AZT), dideoxyinosine (ddI), dideoxycytidine (ddC), and others have been approved by FDA in the United States, but they failed to exhibit complete therapeutic effects without severe adverse side effects. Thus, the development of novel medicaments has become the critical issue.

As another therapeutic agent, protease inhibitors of HIV are known. The Protease inhibitors have been developed based on the fact that the HIV replication could be interrupted by the inhibition of its proteases, during the process that precursor proteins, such as gag and gag-pol polyproteins, comprising capsid proteins and various enzymes fused together are formed and are then cleaved into individual functional proteins, proteases, reverse-transcriptases, and integrases by proteases. Examples of protease inhibitors, used as therapeutic agents for ADIS, include saquinavir, ritonavir, indinavir, and the like. However, the agents have side effects such as diabetes, hemolysis, hemorrhage, hyperlipidemia, impaired lipid metabolism, and others, and causes serious problem of the emergence of tolerant cell lines due to the long-term administration.

The present inventors have endeavored to develop a natural product-derived composition having excellent preventive or therapeutic effects on AIDS (acquired immunodeficiency syndrome), and have achieved the present invention by confirming that a cell line derived from the cambium of *Panax ginseng* including wild ginseng and ginseng, and a lysate, an extract and a culture thereof have excellent preventive and therapeutic effects on AIDS (acquired immunodeficiency syndrome).

SUMMARY OF THE INVENTION

It is an object of the present invention to provide a natural product-derived compound for the prevention and treatment of acquired immunodeficiency syndrome (AIDS) having a minimized adverse side effects compared to prior therapeutic agents.

In accordance with one aspect of the present invention, there is provided a composition for preventing or treating acquired immunodeficiency syndrome (AIDS), comprising one or more of the following: a cell line, and a lysate, an extract and a culture thereof, wherein the cell line is derived from the cambium of *Panax ginseng* and has the following characteristics:

(a) it is in an innately undifferentiated state;
(b) it is a homogeneous cell line; and
(c) it is morphologically characterized by multiple vacuoles.

In accordance with another aspect of the present invention, there is provided a functional food for preventing or ameliorating acquired immunodeficiency syndrome (AIDS), comprising one or more of the following: the cell line, and a lysate, an extract and a culture thereof.

In accordance with another aspect of the present invention, there is also provided an immune enhancing agent for increasing T cells, comprising one or more of the following: the cell line, and a lysate, an extract and a culture thereof.

In accordance with another aspect of the present invention, there is also provided a use of any one or more of the cell line, a lysate, an extract and a culture thereof, for preventing or treating acquired immunodeficiency syndrome (AIDS).

In accordance with another aspect of the present invention, there is also provided a method for preventing or treating acquired immunodeficiency syndrome (AIDS), comprising a step of applying one or more of the following: the cell line, and a lysate, an extract and a culture thereof.

Other features and embodiments of the present invention will be apparent from the following description and the appended claims.

DETAILED DESCRIPTION OF THE INVENTION

Unless otherwise defined, all of technical and scientific terms used herein have the same meanings as commonly understood by one of ordinary skill in the art. Generally, the nomenclature used herein is well known in the art and commonly used.

The definitions of various terms used in the detailed description of the present invention are as follows.

The term "cambium" as used herein refers to a tissue that thickens the stem and the root to allow a plant to grow volumetrically. It was reported that when the cambium where the cell division occurs most actively, is used as an explant for plant tissue culture, a rapid and mass production of cells is possible (Korean Patent No. 0533120).

The term "lysate" as used herein refers to a cell lysate obtained by disrupting cells through a chemical method, e.g., by using a detergent, a physical method, or others. Further, the term "extract" of a cell line as used herein refers to a substance obtained by dissolving cells in a solvent, which may be then concentrated through distillation or evaporation. In addition, the term "culture" as used herein is intended to embrace a cultured cell line and a culture media thereof, wherein the cultured cell line include all cell lines which are differentiated from the staring cell line or which have enhanced potentials for production and secretion of useful materials, according to the culture conditions.

The term "innately undifferentiated" as used herein refers to cells that have not become an undifferentiated state through a dedifferentiation process, but are originally maintained in a pre-differentiated state.

The term "T cell" as used herein refers to a lymphocyte derived from thymus, which play a central role in cell-mediated immunity. In particular, CD4+ T cells which express the CD4 antigen on their surface are called as helper T cells, and CD8+ T cells which express the CD8 antigen, as cytotoxic T cells. The helper T cells assist B cells with their antibody production or cytotoxic T cells with their activation.

In one aspect, the present invention is directed to a composition for preventing or treating acquired immunodeficiency syndrome (AIDS), comprising one or more of the following: a homogenous cell line derived from the cambium of *Panax ginseng*, and a lysate, an extract and a culture thereof as an active ingredient. In the present invention, *Panax ginseng* includes wild ginseng or ginseng (Lian M. L. et al., *J. Plant Biology*, 45: 201, 2002; Han J. Y. et al., *J. Plant Biology*, 49:26, 2006; Teng W. L. et al., *Tissue and Organ Culture*, 68:233, 2002), said wild ginseng or ginseng including open field ginseng or tissue-cultured ginsengs (adventitious roots and cell lines derived therefrom).

The cell line derived from the cambium of *Panax ginseng* according to the present invention has the following characteristics: (a) it is in an innately undifferentiated state; (b) it is a homogeneous cell line; and (c) it is morphologically characterized by multiple vacuoles. The cell line is additionally characterized in that (a) it is present as single cell level during a suspension culture; (b) it has a lower sensitivity to shear stress in a bioreactor, compared to cell lines derived from tissues other than the cambium of *Panax ginseng*; and (c) its growth rate is higher than those of cell lines derived from tissues other than the cambium of *Panax ginseng* and is cultured stably.

In the present invention, the homogenous cell line is obtained by using an isolation method comprising the steps of:

(a) obtaining a *Panax ginseng* cambium-containing tissue;

(b) culturing the cambium-containing tissue in a medium supplemented with IAA (indole-3-acetic acid) or IBA (indole-3-butyric acid) to induce a cell line derived from the cambium, wherein an osmotic stress is applied to the cambium-containing tissue before, during, or after the culture; and (c) collecting the induced, cambium-derived cell line.

In step (b), the osmotic stress is used to induce a cambium-specific cell line, and is applied before the culturing to allow tissues other than cambium, i.e., cortex, phloem, xylem, or pith, to lose differentiation potential, thereby leading to necrosis when cultured with hormones specific to cambium division, e.g., IAA and IBA. At this time, preferably, an osmotic agent may be treated in a concentration of 0.5~2M, the osmotic stress may be maintained for 16 to 24 hours under refrigeration or at room temperature, and then the treated osmotic stress may be removed. However, the concentration of the osmotic agent, treatment time, and temperature may be varied depending upon a plant or tissue used and thus not limited thereto. Further, in step (b), IAA or IBA is preferably contained in an amount of 0.1~5 mg/l.

In addition, said step (c) is preferably performed by proliferating the induced cambium-derived cell line in a medium which contains one or more of 2,4-D (2,4-dichlorophenoxyacetic acid), picloram and IBA, and then collecting the cambium-derived cells. 2,4-D, picloram or IBA is preferably used in an amount of 1~5 mg/L, and, more preferably, 2 mg/L.

The medium used in the present invention may be any conventional medium for plant tissue culture, and examples thereof include, but are not limited to, N6 medium, SH medium, MS medium, AA medium, LS medium, B5 medium, WPM medium, LP medium, White medium, GD medium, DKW medium, DCR medium, etc.

In the present invention, the extract is obtained using a solvent selected from the group consisting of distilled water, lower alcohol, acetone, DMSO (dimethyl sulfoxide) and a mixture thereof. The lower alcohol refers to an alcohol having carbon numbers ranging from 1 to 5 such as methanol, ethanol, and the like.

CD4+ T cells specifically recognize an antigen encountered within the body and then proliferate, while releasing various proteins known as lymphokines which control other cells of the immune system. Further, according to signaling by CD4+ T cells, B lymphocytes recognize an antigen to secrete specific antibodies for neutralizing or eliminating antigenic bacteria and viruses which travel along intercellular fluid. Similarly, according to the signaling from CD4+ T cells, CD8+ T cells (cytotoxic T cells) are activated to kill the cells infected with intracellular pathogens. Besides, CD4+ T cells regulate the activation of cells of the immune system, known as natural killer cells and macrophages, the activation being concomitant with a response to infection and initial malignant tumor.

Immunodeficiency of AIDS explicitly explains the importance of these CD4+ T cells and, due to the loss of these cells, the response of CD4+ T cells, which remain in AIDS patients, to the antigen becomes decreased or eliminated, leading to aberrant generation of essential immune-modulating factors. Because of the decreased number and functional volume of CD4+ T cells, it became impossible to fulfill their essential roles of being directly provided for the maturation of B cells and cytotoxic T cells (CD8+ T cells). Thus, CD4+ T cell count or percentage is measured for monitoring HIV-infected patients (Giorgi J. V. et al., *Clin. Immunol. Newslett.*, 10:55, 1990).

Here, in Examples of the present invention, it was confirmed that the administration of a homogenous cell line derived from the cambium of wild ginseng to patients diagnosed with acquired immunodeficiency syndrome (AIDS) increased the count of helper T cell, CD4+ T cell. Thus, the homogenous cell line of the present invention derived from the cambium of *Panax ginseng* was shown to augment the immunity reduced by HIV viruses, and thus to have preventive and therapeutic effects on AIDS.

In addition, in other Examples of the present invention, the homogenous cell line derived from the cambium of wild ginseng was administered to patients diagnosed as AIDS, and then RNA level of HIV in plasma was measured. As a result, RNA level of HIV was significantly decreased by such administration, and an HIV-undetected patient was also found. This decrease and non-detection of HIV indicate the inhibitory effect on HIV proliferation or virucidal effect on HIV of the homogenous cell line according to the present invention, and demonstrate a treatment effect of the cell line on AIDS. In particular, non-detection of HIV as a result of administration of the homogenous cell line according to the present invention is remarkable as a AIDS therapeutics, suggesting the possibility of permanent cure for AIDS.

While no particular Example is presented with regard to the preventive and therapeutic effects on AIDS of a composition comprising a lysate or an extract of the inventive homogenous cell line, it would be obvious to one of skill in the art that the composition comprising a lysate or an extract of the homogenous cell line would have same or similar effects as the cell line as shown above.

The composition for preventing or treating AIDS, comprising one or more of the homogenous cell line, and the lysate, the extract and the culture thereof, or the immune enhancing agent for increasing CD4+ T cells may be provided as a pharmaceutical composition containing one or more of said homogenous cell line, and the lysate, the extract and the culture thereof alone or in combination with at least one pharmaceutically acceptable carrier, excipient, or diluent. The homogenous cell line, and the lysate, the extract and the culture thereof may be contained in the pharmaceutical composition in a pharmaceutically effective amount, depending upon disease and its severity, the patient's age, weight, health condition and sex, the route of administration and the period of treatment.

The phrase "pharmaceutically acceptable composition" as used herein refers to a composition which is physiologically acceptable and does not cause gastric disorder, allergic responses such as vertigo, or similar responses, when administered to humans. Examples of the carrier, excipient, or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oils.

The pharmaceutical composition may further comprise fillers, anti-coagulating agents, lubricants, wetting agents, perfumes, emulsifying agents, and preservatives. In addition, the pharmaceutical composition of the present invention may be formulated using a method well known in the art, such that it can provide the rapid, sustained, or delayed release of the active ingredient after administration to mammals. The formulation may be in the form of powders, granules, tablets, emulsions, syrups, aerosols, soft or hard gelatin capsules, sterile injectable solutions, or sterile powders, etc.

In another aspect, the present invention provides a functional food for preventing or ameliorating AIDS, comprising one or more of the following: the homogenous cell line, and the lysate, the extract and the culture thereof.

The term 'functional food' as used herein refers to a food, the functionality of which has been enhanced by adding the homogenous cell line, or the lysate, the extract or the culture thereof according to the present invention.

EXAMPLES

Hereinafter, the present invention is described in more detail. The following Examples are given for the purpose of illustration only, and are not intended to limit the scope of the invention.

In particular, while the preventive and therapeutic effects on acquired immunodeficiency syndrome (AIDS) were confirmed using a homogenous cell line in the following Examples, it would be readily appreciated by one of ordinary skill in the art that a lysate, an extract, or a culture thereof would also have the same or similar effects as the cell line.

Example 1

Preparation of Homogeneous Cell Line Derived from Cambium of *Panax ginseng*

1-1: Preparation of Plant Materials (1) FIG. 1(*a*)-A shows typical appearance of wild ginseng used in the present invention. Wild ginseng was purchased, washed with running water to remove soil, dirt, or other contaminants on its surface, its main root was again washed with a liquid detergent, and kept in running water. The washed root was placed into a sterilized flask in a clean bench, and then sterilized with 70% ethanol for about 30 sec to 1 min. Then, the tissue was rinsed out with sterile distilled water, and treated with an antiseptic solution containing 1% to 1.5% of sodium hypochlorite (Junsei, Japan) for 5 to 15 min. At this time, several drops of TWEEN® 20 (Polyoxyethylenesorbitan monolaurate, Junsei, Japan) were added to allow the antiseptic solution to effectively penetrate into the tissue. After the process, the main root was rinsed out with sterilized water 3 to 5 times. Then, in order to prevent browning, the sterilized main root was placed in BIM (browning inhibition medium) containing an antioxidant, shook for 30 min to 1 hr, and then placed onto a sterilized filter paper to remove moisture.

The composition and concentration of BIM used are shown in Table 1.

TABLE 1

Composition and concentration of BIM

| Ingredients | Concentration |
|---|---|
| McCown WPM salt | ¼ strength |
| Sucrose | 1% (w/v) |
| PVP(polyvinyl pyrrolidone) | 0.5% (w/v) |
| Ascorbic acid | 100 mg/L |
| Citric acid | 150 mg/L |
| Adjusted to pH 5.8 | |

Here, the salt is added in an amount corresponding to ¼ of the total amount.

Figure 1:
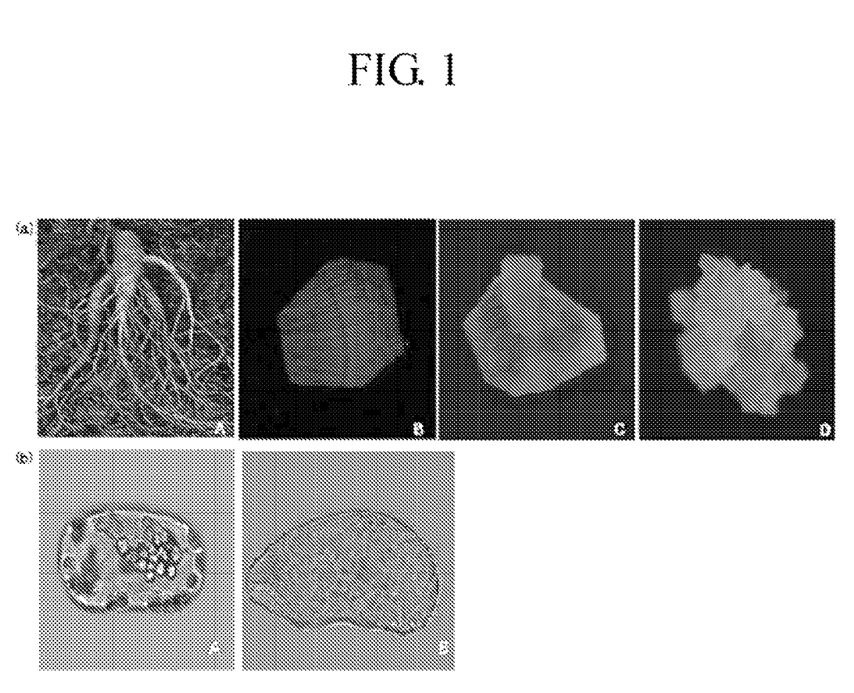
FIG. 1 displays photographs showing a process of cell line induction according to the present invention (a), and photographs showing a cell line derived from the cambium of wild ginseng ((b)-A) and a callus cell line (Korea Research Institute of Bioscience and Biotechnology, KCTC PC10224) derived from the cotyledon of ginseng ((b)-B)

Then, in order to prevent browning the root was placed in a sterilized petri dish containing CS solution (cutting solution, Table 2) supplemented with an antioxidant. The exterior bark of the root was peeled thinly, the resulting root was divided into halves, and sliced off into pieces sized length×width× thickness=0.5~0.7 cm×0.5~0.7 cm×0.2~0.5 mm such that the pieces contained the actively dividing cambium. FIG. 1(a)-B shows an explant which was sliced off into above size to contain the cambium of a main root of wild ginseng.

TABLE 2

CS (cutting solution)

| Ingredients | Concentration |
|---|---|
| PVP(Polyvinyl pyrrolidone) | 0.5% (w/v) |
| Ascorbic acid | 100 mg/L |
| Citric acid | 150 mg/L |

(2) An adventitious root of 100-year old wild ginseng maintained in a bioreactor was prepared, and then subjected to the same process as described above to obtain the cambium-containing explants.

1-2: Treatment of Osmotic Agent on Explants Containing Cambium of Wild Ginseng Main Root Each of explant prepared in Example 1-1 was treated with osmotic stress in order to induce necrosis of differentiated tissues, i.e., xylem, phloem, pith, etc., and only to allow a meristem, the cambium, to survive. The explant was blotted to a pre-culture medium (medium 1, Table 3) covered with a filter paper, placed into a flask containing 1M sucrose (Duchefa, Netherland) solution, and stored under a refrigeration condition for 16~24 hr to apply an osmotic pressure. The explant was then treated with 0.05M sucrose solution for 5 min and again with 0.1M sucrose solution for 5 min to remove the stress by high concentration of sucrose. Then, the explant was placed into a pre-culture medium (medium 1) covered with a filter paper to remove moisture.

TABLE 3

Composition of pre-culture medium (medium 1)

| | Composition | mM | mg/L |
|---|---|---|---|
| Macroelements | Ca(NO$_3$)$_2$ | 2.35 | 471.26 |
| | NH$_4$NO$_3$ | 5 | 400 |
| | MgSO$_4$•7H$_2$O | 1.5 | 180.54 |
| | K$_2$SO$_4$ | 5.68 | 990 |
| | CaCl$_2$•2H$_2$O | 0.65 | 72.5 |
| | KH$_2$PO$_4$ | 1.25 | 170 |
| | | μM | |
| Microelements | MnSO$_4$•4H$_2$O | 131.94 | 22.3 |
| | ZnSO$_4$•7H$_2$O | 29.91 | 8.6 |
| | Na$_2$MoO$_4$•2H$_2$O | 1.03 | 0.25 |
| | H$_3$BO$_3$ | 100.27 | 6.2 |
| | CuSO$_4$•5H$_2$O | 1.0 | 0.25 |
| | FeNa-EDTA | 100 | 36.7 |
| Vitamin | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 2.96 | 1.0 |

1-3: Induction of Homogenous Cell Line from an Explant Containing Cambium of Wild Ginseng In order to induce a cambium-derived homogenous cell line having a division potential, the explant treated with osmotic stress in Example 1-2 was plated in a medium for cell line induction (medium 2, Table 4). The medium used in the plating is shown in Table 4. The plated explant was cultured under a dark condition of 22±1° C.

TABLE 4

Composition of a medium for inducing cambium-derived homogenous cell line induction

| Composition and condition | Concentration used and condition |
|---|---|
| Salt | Full strength WPM |
| Sucrose | 3% (w/v) |
| IAA(indole-3-acetic acid) | 2 mg/L |
| pH | 5.8 |
| Gelrite | 0.3% (w/v) |
| Ascorbic acid | 100 mg/L |
| Citric acid | 150 mg/L |

At this time, the explant plated onto the medium for inducing a cell line fastly showed a yellow color around cambium in the early stage within 2~3 days and the color spread out into whole explant depending on time. For the purpose of continuously inducing a homogenous cell line and continuously proliferating it, the explant showing yellow response around cambium was sub-cultured in an optimum medium for isolating and proliferating a cambium-derived homogenous cell line which has a division potential (medium 3), but browning was intensified and no response other than browning response appeared over time.

In contrast, it was observed that the explant plated onto the medium for homogenous cell line after the induction and removal of the osmotic stress showed no induction of homogenous cells from tissues other than cambium. That is, in case of the explant plated after the osmotic treatment and removal, the cambium of the explant began to turn into light yellow in 3~7 culture days. About 7~14 days thereafter, it was also observed that a round cell line was induced in the region of light yellow. Meanwhile, same results were observed in both explants containing the cambium of open field true wild ginseng or wild ginseng adventitious root. FIG. 1(a)-C shows the appearance of the homogenous cell line having cambium-specific division potential among cambium-containing explants of wild ginseng.

Meanwhile, when the explant with osmotic treatment was cultured in a conventional medium containing 2,4-D, which is typically used in the culture of *Panax ginseng*, e.g., ginseng, wild ginseng, etc., not in the medium for homogenous cell line induction, it was observed that whole explant began to turn into yellow in 7~10 days and a cell line was induced from whole sliced surface about 7~14 days thereafter.

TABLE 5

Comparison of responses between explants with or without osmotic treatment

| Treatment type | Untreated | 16 hr-treated | 20 hr-treated | 24 hr-treated |
|---|---|---|---|---|
| Aspect | At the initial stage after the inoculation, a yellow reaction progressed and had the tendency to spread throughout the entire explant. Then, a severe browning color reaction progressed throughout the explants including the cambium, and the induction of a homogeneous cell line, specific in the cambium, was no longer shown | Induction of cells was observed specifically in cambium. As a result of treatment of osmotic stress for varying time, similar results were observed. That is, there was no significant difference depending on time. | | |

1-4: Proliferation of Isolated Homogenous Cell Line Derived from Wild Ginseng Cambium The homogenous cell line induced in Example 1-3, which has a division potential derived from cambium, were used for proliferation. The medium shown in <Table 7> based on salt composition as set forth in <Table 6> was used as an optimum medium for homogenous cell line proliferation. In <Table 7>, 2,4-D was used for proliferation of homogenous cell line induced from the cambium of open field true wild ginseng, and IBA, for that of homogenous cell line induced from the adventitious root of wild ginseng.

TABLE 6

Basic salt composition of optimum medium for isolating and proliferating homogenous cell line derived from cambium

| Composition | | mM | mg/L |
|---|---|---|---|
| Macroelements | $CaCl_2 \cdot 2H_2O$ | 2.99 | 332.02 |
| | $KH_2PO_4$ | 1.25 | 170 |
| | $KNO_3$ | 18.79 | 1900 |
| | $MgSO_4$ | 1.5 | 180.54 |
| | $NH_4NO_3$ | 20.61 | 1650 |
| | | uM | |
| Microelements | $CoCl_2 \cdot 6H_2O$ | 0.11 | 0.025 |
| | $CuSO_4 \cdot 5H_2O$ | 0.1 | 0.025 |
| | FeNa-EDTA | 100 | 36.7 |
| | $H_3BO_3$ | 100.27 | 6.2 |
| | KI | 5.0 | 0.83 |
| | $MnSO_4 \cdot 4H_2O$ | 100 | 16.9 |
| | $Na_2MoO_4 \cdot 2H_2O$ | 1.03 | 0.25 |
| | $ZnSO_4 \cdot 7H_2O$ | 29.91 | 8.6 |
| Vitamins | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 0.3 | 0.1 |

TABLE 7

Composition of optimum medium for isolating and proliferating homogenous cell line derived from cambium (medium 3)

| Composition and condition | Concentration used and condition |
|---|---|
| Salt | Full strength MS |
| Sucrose | 3% (w/v) |
| IBA (indole-3-butyric acid) or 2,4-D (2,4-dichlorophenoxyacetic acid) | 2 mg/L |
| pH | 5.8 |
| Gelrite | 0.3% (w/v) |
| Ascorbic acid | 100 mg/L |
| Citric acid | 150 mg/L |

As shown in FIG. 1(a)-C, the sub-culture in medium 3 as set forth in <Table 8>, after induction of cambium-specific homogenous cell line using osmotic stress treatment and medium 2, made it possible to isolate homogenous cell line having a division potential derived from cambium after 10~20 days culture. The homogenous cell line derived from the wild ginseng cambium was again cultured in the same medium to proliferate the homogenous cell line having a division potential. FIG. 1(a)-D is the appearance of the homogenous cell line specifically derived from cambium, when proliferated in the medium 3 as set forth in <Table 7>.

1-5: Observation of Characteristics of Isolated Cell Line

The homogenous cell line derived from the wild ginseng cambium was placed in a flask filled with a liquid medium of <Table 8> and cultured under a dark condition in a 25±1° C., 100 rpm, rotary shaker. The sub-culture period was fixed into 2 weeks to allow the culture cell to maintain high vitality at logarithmic growth phase. In <Table 8>, 2,4-D was used for the proliferation of homogenous cell line derived from the cambium of open field true wild ginseng and IBA, for that of homogenous cell line derived from the adventitious root of wild ginseng.

Meanwhile, a callus derived from the ginseng cotyledon was cultured in medium 4 of <Table 8> and compared with the homogenous cell line derived from the wild ginseng cambium according to the present invention.

TABLE 8

Suspension medium in *Panax ginseng*. (medium 4)

| Composition and condition | Concentration and condition |
|---|---|
| Salt | Full strength MS |
| Sucrose | 3% (w/v) |
| IBA (indole-3-butyric acid) or 2,4-D (2,4-dichlorophenoxyacetic acid) | 2 mg/L |
| pH | 5.8 |

First, as a result of observation of the degree of cell aggregation using biological microscope CX31 (Olympus, Japan), 95% or more of the cell line derived from the cambium of open field true wild ginseng, which was treated with 2,4-D, were present as single cell level in suspension culture, and 60% or more of the cell line derived from the cambium of adventitious root, which was treated with IBA, were also present as single cell level, confirming that the cell lines of the present invention have a characteristic of being present as single cell level in suspension culture. In addition, as shown in FIG. 1(b)-A, both cell lines, which were derived from the cambium derived from open field true wild ginseng treated with 2,4-D or from adventitious root treated with IBA respectively, were shown to have multiple small vacuoles and to be in an undifferentiated state. However, in case of a callus derived from the ginseng cotyledon (Korea Research Institute of Bioscience and Biotechnology, KCTC PC10224), no multiple and small vacuoles were observed and, instead, one large vacuole was observed, as shown in FIG. 1(b)-B.

TABLE 9

Type of cell aggregates of *Panax ginseng* long-term cultures

| Large cell aggregates | Moderate cell aggregates | Small cell aggregates | Single cell population | Explant source |
|---|---|---|---|---|
| 90% | 7% | 2% | 1% | Cotyledon |
| 0 | 0 | 5% | 95% | Cambium (2,4-D treatment) |
| 5% | 10% | 25% | 60% | Cambium (IBA treatment) |

Large cell aggregates, size higher than $1.5 \times 10^3$ μm;
Moderate cell aggregates $1 \times 10^3$ μm;
Small cell aggregates $4 \times 10^2$ μm $<$ size $< 1 \times 10^3$ μm In the meantime, in order to examine the possibility of mass culture, a callus derived from the cotyledon of wild ginseng and homogenous cell derived from the cambium of wild ginseng according to the present invention were each cultured in an airlift bioreactor (Sungwon high-tech, Korea). The medium of <Table 8> was used, and the culture was maintained at 25±1° C. under a dark condition As a result, while the doubling time of the culture derived from the cotyledon of ginseng was 21 days in a flask, it increased to 28 days in the reactor. It was considered that the generation of growth ring in a reactor, aggregation of a plant culture on culture, and the sensitivity to shear stress due to rigid cellular membrane would contribute to the decreased cell viability.

Meanwhile, the doubling time was 3~4 days for a culture of cells derived from the cambium of open field true wild ginseng treated with 2,4-D according to the present invention and the doubling time was 5~6 days for a culture of cells derived from the cambium of wild ginseng adventitious root treated with IBA, both of which was little different or rather shortened between both in a flask and a reactor. The culture of homogenous cells derived from the cambium formed very small area of growth ring, the rings of inner wall were conveniently removed when the medium is moved by simple stimuli. Further, as the cell lines have small aggregation, small cell size, multiple vacuoles, low sensitivity to shear stress, thereby do not bring about the decrease in cell viability. That is, it was confirmed that the homogenous cell line derived from the cambium according to the present invention has low sensitivity to shear stress gained from stirring action in a bioreactor for mass culture, thus being capable of rapid mass growth. Thus, it was shown that the homogenous cell line derived from the cambium according to the present invention has the sensitivity of 5~9 times lower than cell lines derived from tissues other than cambium

TABLE 10

Doubling times of homogenous cell line derived from wild *ginseng* cambium and cells derived from *ginseng* cotyledon in liquid suspension culture and bioreactor.

| Explant source | Doubling time (day) | |
|---|---|---|
| | flask | Bioreactor |
| Cotyledon | 21 | 28 |
| Cambium (2,4-D treatment) | 5 | 3~4 |
| Cambium (IBA treatment) | 7 | 5~6 |

Meanwhile, a heterogenous cell line, a callus derived from the ginseng cotyledon (Korea Research Institute of Bioscience and Biotechnology, KCTC PC10224) and a homogenous cell line derived from the cambium were cryopreserved. The culture from 6 days to 8 days was used as the suspension culture, and a cryopreservative was a medium containing 0.5M glycerol (DUCHEFA, The Netherlands), 0.5M DMSO (DUCHEFA, The Netherlands), and 1M sucrose (DUCHEFA, The Netherlands) and was transferred to 5 ml cryovial (Duran, USA). The amount of cell inoculation treated to the cryopreservative is 200 mg/ml. The suspension cells treated with the preservative were kept for 30 minutes in a refrigerator, stored for 3 hours in a deep freezer, followed by immersing in liquid nitrogen.

Then, the cultured cells kept for 20 min in liquid nitrogen were immersed into a 40° C. water bath for 1-2 min to thaw. The cell suspension was filtered through a sterile funnel and a filter paper for cell re-growth. The filtered cells were placed onto a solidified growth medium containing a filter paper and stabilized for 30 min in a room temperature, followed by transferring to a fresh solidified growth medium.

As a result, a heterogeneous cell line derived from the ginseng cotyledon did not re-grow, while a homogeneous cell line derived from the ginseng cambium started to re-grow after 4 weeks. There was no difference in proliferation ratio between before and after cryopreservation.

Example 2

Drying of Homogeneous Cell Line Derived from Wild Ginseng Cambium and Preparation of Extract Thereof The homogeneous cell line derived from the cambium of wild ginseng adventitious root of Example 1 was dried and extracted as follows:

(1) Preparing dried cell line;
(i) The cell line isolated from culture medium was freeze dried or hot-air dried;
(ii) The cell line was pulverized using a pulverizer.
(2) Preparation of extract using distilled water
(i) 500 g of the cell lines, which were isolated from culture medium, were hot-air dried, or were freeze dried, were extracted with 5000 ml of distilled water while shaking for 6 hour at 50° C.;
(ii) After said dissolution, the extract was centrifuged at 3,000 g for 10 min and the supernatant was collected to obtain a distilled water-soluble product; and (iii) The distilled water-soluble product was concentrated under a reduced pressure using a rotary vacuum concentrator.

(3) Preparation of extract using ethanol (i) 500 g of the cell lines, which were isolated from culture medium, were hot-air dried, or were freeze dried, were extracted with 5000 ml of ethanol while shaking for 6 hour at 50° C.;

(ii) After said dissolution, the extract was centrifuged at 3,000 g for 10 min and the supernatant was collected to obtain an ethanol-soluble product; and (iii) The ethanol-soluble product was concentrated under a reduced pressure using a rotary vacuum concentrator.

Experimental Example 1

Verification on Preventive and Therapeutic Effects of Homogeneous Cell Line Derived from Cambium of *Panax ginseng* on Acquired Immunodeficiency Syndrome (i)—Measurement of Cell Count Ratio of CD4+ T/CD8+ T In order to verify the preventive and therapeutic effects of homogenous cell line derived from the cambium of *Panax ginseng* according to the present invention, the dried cell line powder prepared from Example 2(1) was administered to an AIDS patient (born in 1976, male, diagnosed with AIDS in August, 2006) with a positive HIV response. One gram of the powder was orally administered as a dissolved form in water for 9 days (date of initial administration: 19 Aug. 2008) three times a day. The patient was required not to take any other therapeutic agent for AIDS, and there was no adverse side effect shown.

After 9 days of administration, blood sample was taken from the patient, and then incubated with Simultest reagent (Becton dichknson, San Jose, Calif.) using phycoerythrin-conjugated antibodies against CD4 antigen and fluoresein isothiocyanate-conjugated antibodies against CD8 antigen. After staining CD4+ and CD8+ T cells in accordance with the above method, stained cells were measured using the FACscan flow cytometer (Becton-Dickinson) according to the manufacturer's instruction. The ratio of CD4+ T cell count/CD8+ T cell count was calculated based on the respective cell count as obtained.

shown that the administration of homogeneous cell line derived from the cambium of wild ginseng also increased CD8+ T cell count.

Meanwhile, the ratio of CD4+ T cell count/CD8+ T cell count became closer to 1 after administration than before administration. Typically, the ratio of CD4+ T cell count/CD8+ T cell count is about 1 in a normal person. In contrast, for AIDS patients, CD4+ T cell count absolutely decreases, and CD8+ cell count increases due to immune hyperactivation in initial AIDS, but gradually decreases. Accordingly, in the initial AIDS, the ratio of CD4+ T cells to CD8+ T cells showed a tendency to decrease and then appeared to change.

In above experimental results, the ratio of CD4+ T cell count/CD8+ T cell count rather decreased just before administration, but it seems to be owing to the dramatic drop of CD8+ T cell count before administration. After administration, the ratio increased within normal range, which indicates that the immunity against HIV generally increased.

Therefore, the homogeneous cell line derived from the cambium of wild ginseng was found to enhance the immunity reduced by HIV and to have preventive and therapeutic effects on acquired immunodeficiency syndrome (AIDS).

Experimental Example 2

Verification on Preventive and Therapeutic Effects of Homogenous Cell Line Derived from Cambium of *Panax ginseng* on Acquired Immunodeficiency Syndrome (ii)—Measurement of CD4+ T Cell Level In order to verify the preventive and therapeutic effects of homogenous cell line derived from the cambium of *Panax ginseng* according to the present invention on acquired immunodeficiency syndrome, the freeze dried cell line powder prepared from Example 2(1) was administered to additional AIDS patients with a positive HIV response. One gram of the powder was orally administered as a dissolved form in water three times a day (morning, noon, evening). The patient was required not to take any other therapeutic agent for AIDS, and there was no adverse side effect shown.

The period of administration was different between patients. After administration, 2~3 mL of blood sample was taken from each patient and BD MultiTEST™ reagent (CD3

TABLE 11

| | | Clinical case 1 | | | | | | | | | | | |
|---|---|---|---|---|---|---|---|---|---|---|---|---|---|
| Test item | Reference value | 2007 0502 | 2007 0627 | 2007 0829 | 2007 1024 | 2007 1226 | 2008 0227 | 2008 0430 | 2008 0603 | 2008 0617 | 2008 0702 | 2008 0730 | 2008 0827 |
| Test interval(day) | | | 56 | 63 | 56 | 63 | 63 | 63 | 34 | 14 | 15 | 28 | 28 |
| CD4+ T | 500~1500 cells/μl | 431 | 390 | 490 | 448 | 387 | 397 | 350 | 403 | 352 | 408 | 280 | 616 |
| CD8+ T | 800~1200 cells/μl | | | | | | | | 762 | 581 | 756 | 384 | 1000 |
| CD4/CD8 | 1 | | | | | | | | 0.53 | 0.61 | 0.54 | 0.73 | <0.62 |

Date of initial administration: 19 Aug. 2008

Figure 2:
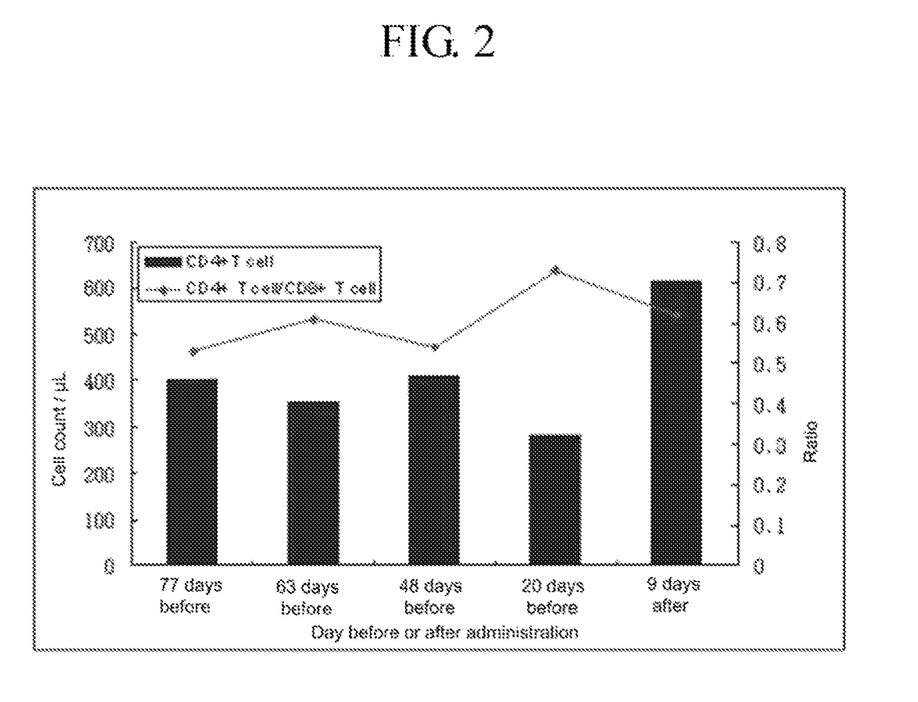
FIG. 2 presents a graph showing CD4+ T cell count and the ratio of CD4+ T cell count/CD8+ T cell count, measured from 77 days before administration to 9 days after administration of the inventive cell line derived from the cambium of wild ginseng.

As shown in Table 11 and FIG. 2, CD4+ T count after administration was 616 cells/μL, confirming that it reached to normal value based on reference value. That is, it was shown that the administration of homogeneous cell line derived from the cambium of wild ginseng increased CD4+ T cell count.

In addition, CD8+ T cell count measured was at a very small level, 384 cells/μL, before administration, but it reached within normal range after administration. Therefore, it was fluorescein isothiocyanate antibody (FITC), CD8 phycoerythrin antibody (PE), CD45 peridinin-chlorophyll protein antibody (PerCP), CD4 allophycocyanin antibody (APC); Becton-Dickinson, Britain) was added to each sample to allow each fluorescence-labeled antibody to bind with a blood cell surface antigen, followed by measuring CD4 levels using the Facs CD4 machine (BD, Britain) according to the manufacturer's instruction.

The measurement results and period of administration for each patient are as follows.

TABLE 12

| Clinical case 2 (SEX/BIRTH: F/49; nationality: Ghana; date of initial administration: 2009 Jul. 29) | | |
|---|---|---|
| Time | Date | CD4 count ($\times 10^5$/L) |
| before | 2009 Jul. 28 | 180 |
| 1st | 2009 Aug. 5 | 500 |

For patients of clinical case 2, while there was no severe symptom caused by AIDS except for cough, headache, diarrhea, hypertension, and red spots for 3 months before administration, these symptoms were alleviated after administration. In addition, the level of CD4+ T cells was very low, 180, before administration, but it increased to a normal range, 500, after administration.

The immunodeficiency of AIDS are expressed as aberrant generation of essential immune-modulating factors which results from the decrease or elimination of CD4+ T cell response to the antigen remaining in AIDS patients, due to the loss of CD4+ T cells. The treatment progress is verified by measurement of CD4+ T cell the count or percentage, and accordingly the increase in CD4+ T cells above shows that the homogenous cell line is effective in the treatment of AIDS.

TABLE 13

| Clinical case 3 (SEX/BIRTH: M/32; nationality: Ghana; date of initial administration: 2009 Sep. 10) | | |
|---|---|---|
| Time | Date | CD4 count ($\times 10^5$/L) |
| before | 2009 Sep. 9 | 260 |
| 1st | 2009 Sep. 16 | 316 |

For a patient of clinical case 3 which had not received ARV (anti-retro virus) since diagnosed with AIDS, CD4 count increased from 260 to 316 for a short term after administration. The increase in CD4+ T cells indicates that the homogenous cell line according to the present invention is useful in the treatment of AIDS.

TABLE 14

| Clinical case 4 (SEX/BIRTH: F/31; nationality: Ghana; date of initial administration: 2009 Jun. 20) | | |
|---|---|---|
| Time | Date | CD4 count ($\times 10^5$/L) |
| before | 2009 Jun. 19 | 282 |
| 1st | 2009 Jul. 17 | 320 |

For a patient of clinical case 4, CD4+ T cell count increased from 282 to 320, the increase in CD4+ T cells indicating that the homogenous cell lines according to the to present invention are useful in the treatment of AIDS.

TABLE 15

| Clinical case 5 (SEX/BIRTH: M/38; nationality: Ghana; date of initial administration: 2009 Jun. 20) | | |
|---|---|---|
| Time | Date | CD4 count ($\times 10^5$/L) |
| before | 2009 Jun. 19 | 443 |
| 1st | 2009 Jul. 17 | 485 |
| 2nd | 2009 Sep. 8 | 559 |

For a patient of clinical case 5, CD4+ T cell count continuously increased from 443 to 559, and the increase in CD4+ T cells indicates that the homogenous cell line according to the present invention is useful in the treatment of AIDS.

TABLE 16

| Clinical case 6 (SEX/BIRTH: M/45; nationality: Ghana; date of initial administration: 2009 Aug. 12) | | |
|---|---|---|
| Time | Date | CD4 count ($\times 10^5$/L) |
| before | 2009 Aug. 11 | 484 |
| 1st | 2009 Aug. 19 | 527 |
| 2nd | 2009 Sep. 9 | 613 |

For a patient of clinical case 6, CD4+ T cell count continuously increased from 484 to 613, and the increase in CD4+ T cells indicates that the homogenous cell line according to the present invention is useful in the treatment of AIDS.

TABLE 17

| Clinical case 7 (SEX/BIRTH: F/45; nationality: Ghana; date of initial administration: 2009 Jun. 24) | | |
|---|---|---|
| Time | Date | CD4 count ($\times 10^5$/L) |
| before | 2009 Jun. 23 | 690 |
| 1st | 2009 Jul. 8 | 1073 |

For a patient of clinical case 7, conventional symptoms accompanying with AIDS, e.g., chronic cough, anemia, etc., were eased with administration, and CD4+ T cell count significantly increased from 690 to 1073.

In conclusion, the homogenous cell line derived from the cambium of *Panax ginseng* according to the present invention was confirmed to increase CD4+ T cell count. Considering that the immunodeficiency of AIDS are expressed as aberrant generation of essential immune-modulating factors which results from the decrease or elimination of CD4+ T cell responses to the antigen remaining in AIDS patients, due to the loss of CD4+ T cells, the homogenous cell line derived from the cambium of wild ginseng is effective in the treatment of AIDS.

Experimental Example 3

Verification on Preventive and Therapeutic Effects of Homogenous Cell Line Derived from Cambium of *Panax ginseng* on Acquired Immunodeficiency Syndrome (iii)—Measurement of RNA Level of HIV In order to verify the preventive and therapeutic effects of homogenous cell line derived from the cambium of *Panax ginseng* according to the present invention on acquired immunodeficiency syndrome, patients with a positive HIV response were additionally measured for RNA levels of HIV using RT-PCR.

In similar manner to Experimental Example 3, the freeze-dried cell line powder prepared from Example 2(1) was administered to AIDS patients. One gram of the powder was orally administered as a dissolved form in water three times a day (morning, noon, evening). The patient was required not to take any other therapeutic agent for AIDS, and there was no adverse side effect shown.

The period of administration was different between patients. After administration, blood sample was taken from each patient and plasma was obtained therefrom, followed by quantitative RT-PCR using COBAS® AmpliPrep/COBAS® TaqMan® HIV-1 Test, version 2.0[v2.0] from Roche (Switzerland) according to the manufacturer's instruction. At this time, the quantification of HIV-1 RNA was carried out using COBAS® TaqMan® Analyzer or COBAS® TaqMan® 48 Analyzer from Roche (Switzerland). Meanwhile, some patients were also measured for CD4+ T cell levels using a same way as Example 2.

The measurement results and period of administration for each patient are as follows.

TABLE 18

Clinical case 8 (SEX/BIRTH: M/51; nationality: Kenya; date of initial administration: 2009 Jun. 20)

| Time | Date | HIV-1 RNA (copies/mL) (normal range: undetected) |
|---|---|---|
| Before | 2009 Jun. 19 | 6,252 |
| 1st | 2009 Jul. 2 | 3,574 |

For a patient of clinical case 8 which had not received ARV (anti-retro virus) since diagnosed with AIDS, HIV-1 RNA level dramatically decreased from 6,252 to 3,573 in a first test.

This dramatic decrease in HIV indicates that the homogenous cell line according to the present invention has an inhibitory or cytotoxic effect on HIV, and that they may be effectively used as a composition for treating or preventing AIDS.

TABLE 19

Clinical case 9 (SEX/BIRTH: F/38; nationality: Ghana; date of initial administration: 2009 Sep. 10)

| Time | Date | CD4 count ($\times 10^5$/L) | HIV-1 RNA (copies/mL) (normal range: undetected) |
|---|---|---|---|
| Before | 2009 Sep. 10 | 377 | 1,508 |
| 1st | 2009 Sep. 16 | 380 | 1,675 |
| 2nd | 2009 Sep. 24 | — | 751 |

For a patient of clinical case 9, HIV-1 RNA level slightly increased in a first test, but it was dramatically decreased from 1,508 to 751 in a second test.

The decrease in HIV virus indicates that the homogenous cell lines according to the present invention have an inhibitory or cytotoxic effect on HIV virus, and that they may be effectively used as a composition for treating or preventing AIDS.

TABLE 20

Clinical case 10 (SEX/BIRTH: M/34; nationality: Kenya; date of initial administration: 2009 Jun. 20)

| Time | Date | HIV-1 RNA (copies/mL) (normal range: undetected) |
|---|---|---|
| Before | 2009 Jun. 19 | 18,232 |
| $1^{st}$ | 2009 Jul. 2 | 6,791 |
| $2^{nd}$ | 2009 Jul. 17 | 3,847 |
| $3^{rd}$ | 2009 Sep. 1 | 1,875 |

For a patient of clinical case 10, HIV-1 RNA level in plasma was very high, 18,232 before administration, but it gradually decreased to 1,875 by continuous administration.

The decrease in HIV virus indicates that the homogenous cell line according to the present invention has an inhibitory or cytotoxic effect on HIV, and that they may be effectively used as a composition for treating or preventing AIDS.

TABLE 21

Clinical case 11 (SEX/BIRTH: F/26; nationality: Thailand; date of initial administration: 2009 Jul. 19)

| Time | Date | CD4 count ($\times 10^5$/L) | HIV-1 RNA (copies/mL) (normal range: undetected) |
|---|---|---|---|
| Before | 2009 Mar. 21 | 233 | 36,594 |
| $1^{st}$ | 2009 Sep. 16 | 387 | 30,000 |

For a patient of clinical case 11, the increase in CD4 count and the decrease in HIV-1 RNA were both confirmed, and thus the homogenous cell line according to the present invention may be effectively used as a composition for treating or preventing AIDS.

TABLE 22

Clinical case 12 (SEX/BIRTH: F/35; nationality: Ghana; date of initial administration: 2009 Aug. 12)

| Time | Date | CD4 count ($\times 10^5$/L) | HIV-1 RNA (copies/mL) (normal range: undetected) |
|---|---|---|---|
| Before | 2009 Aug. 10 | 919 | 45,209 |
| $1^{st}$ | 2009 Aug. 19 | 962 | 18,786 |

For a patient of clinical case 12, the increase in CD4 count and the decrease in HIV-1 RNA were both confirmed, and thus the homogenous cell line according to the present invention may be effectively used as a composition for treating or preventing AIDS.

TABLE 23

Clinical case 13 (SEX/BIRTH: F/35; nationality: Ghana; date of initial administration: 2009 Jun. 24)

| Time | Date | CD4 count ($\times 10^5$/L) | HIV-1 RNA (copies/mL) (normal range: undetected) |
|---|---|---|---|
| Before | 2009 Jun. 24 | 414 | — |
| $1^{st}$ | 2009 Jul. 8 | 457 | — |
| $2^{nd}$ | 2009 Jul. 29 | 490 | — |
| $3^{rd}$ | 2009 Aug. 5 | 550 | — |
| 1st | 2009 Sep. 16 | — | 2,709 |
| 2nd | 2009 Sep. 24 | — | 2,540 |

For a patient of clinical case 13, CD4 count gradually increased (only CD4 count was measured during initial administration period), and HIV-1 RNA level decreased by administration (subsequent two time measurement). These indicate that the homogenous cell line according to the present invention may be effectively used as a composition for treating or preventing AIDS.

TABLE 24

Clinical case 14 (SEX/BIRTH: M/46; nationality: Myanmar; date of initial administration: May 2009)

| Period of administration | HIV-1 RNA (copies/mL) (normal range: undetected) |
|---|---|
| about two months | undetected |

Figure 3:
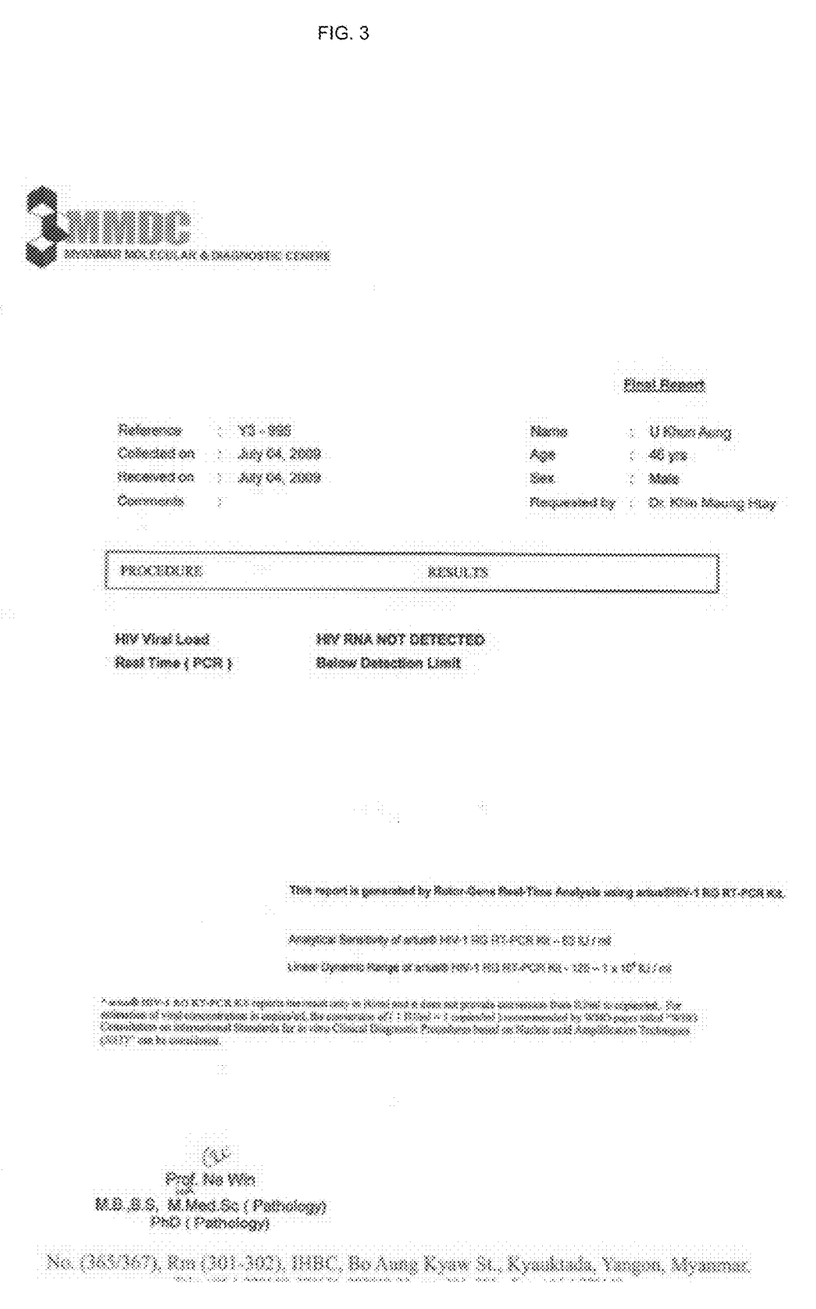
FIG. 3 shows detection results of HIV-1 RNA for a patient of Clinical case 14.

For a patient of clinical case 14, HIV-1 RNA was undetected after about two month administration, as shown in FIG. 3 (For a patient of clinical case 14, Rotor-Gene Real-Time analysis was carried out using Artus® HIV-1 RG RT-PCR kit from QIAGEN (Germany)). The undetected HIV in an AIDS patient by administration of homogenous cell line according to the present invention is remarkable, suggesting the possibility of permanent cure for AIDS.

In conclusion, it was confirmed that the administration of cell lines according to the present invention decreases RNA levels of HIV, in spite of the difference in the width depending on the individuals. The decrease or non-detection of HIV indicates that the homogenous cell line according to the present invention has an inhibitory or cytotoxic effect on HIV, and that they may be effectively used as a composition for treating or preventing AIDS.

Preparation Example 1

Pharmaceutical Formulation

Formulation Example 1

Preparation of Tablet

The cell line extract (100 mg) prepared in Example 2 was mixed with corn starch (100 mg), lactose (100 mg) and magnesium stearate (2 mg) to prepare tablets according to a conventional method.

Formulation Example 2

Preparation of Capsule

The cell line extract (500 mg) prepared in Example 2 was filled into a soft gelatin capsule to prepare capsules.

Formulation Example 3

Preparation of Syrup

The cell line (1 g) prepared in Example 1, high fructose corn syrup (10 g), mannitol (5 g), and appropriate amount of purified water were formulated into 100 mL syrup according to a conventional method.

Formulation Example 4

Preparation of Injectable Formulation

The cell line extract (200 mg) prepared in Example 2 was dissolved in a saline (200 mg) containing polyoxyethylene hydrogenated castor oil while heating to prepare injectable formulations containing the cell line extract in a concentration of 0.1%.

Preparation Example 2

Preparation of Functional Foods—Functional Beverages

Preparation Example 1

The cell line (200 mg) prepared in Example 1 was dissolved in water (96 mL), vitamin C (500 mg) as an adjuvant, citric acid (1 g) as a taste acid, oligosaccharide (1 g), and sodium benzoate (0.05 g) as a preservative were added thereto, and purified water added to make 100 mL, to prepare functional beverages.

Preparation Example 2

The cell line (200 mg) prepared in Example 2 was dissolved in water (96 mL), vitamin C (500 mg) as an adjuvant, citric acid (1 g) as a taste acid, oligosaccharide (1 g), and sodium benzoate (0.05 g) as a preservative were added thereto, and purified water added to make 100 mL, to prepare functional beverages.

INDUSTRIAL AVAILABILITY

As described above, the homogenous cell line, the lysate, the extract, and the culture of, which are derived from a natural product, minimize adverse side effects of prior therapeutic agents and safe for the human body. Further, they effectively increase the count of T cells such as CD4+ T cells and decrease the number of HIVs, thereby preventing opportunistic infection, dysneuria, and neoplaia caused by immune incompetence, and ultimately the risk of death. Therefore, they are useful in preventing and treating acquired immunodeficiency syndrome, and relieving symptoms of AIDS.

Although the present invention has been described by way of a detailed description in which various embodiments and aspects of the invention have been described, it will be seen by one skilled in the art that the full scope of this invention is not limited to the examples presented herein. Therefore, the substantial scope of the present invention will be defined by the accompanying claims and equivalents thereof.

What is claimed is:

1. A method of ameliorating acquired immunodeficiency syndrome (AIDS), the method comprising administering a cell line derived from the cambium of *Panax ginseng*, wherein the cell line has the following characteristics:
   (a) it is in an innately undifferentiated state; and
   (b) it is a homogeneous cell line.

2. The method of claim 1, wherein the cell line further has the following characteristics:
   (a) it is present as single cell level during a suspension culture;
   (b) it has a lower sensitivity to shear stress in a bioreactor, compared to cell lines derived from tissues other than the cambium of *Panax ginseng*; and
   (c) its growth rate is higher than those of cell lines derived from tissues other than the cambium of *Panax ginseng* and is cultured stably.

3. The method of claim 1, wherein the cell line is obtained by using an isolation method comprising the steps of:
   (a) obtaining a *Panax ginseng* cambium-containing tissue;
   (b) culturing the cambium-containing tissue in a medium supplemented with IAA (indole-3-acetic acid) or IBA (indole-3-butyric acid) to induce a cell line derived from the cambium, wherein an osmotic stress is applied to the cambium-containing tissue before, during, or after the culture; and
   (c) collecting the induced, cambium-derived cell line.

4. The method of claim 3, wherein step (c) is performed by proliferating the induced cambium-derived cell line in a medium which contains one or more of 2,4-D (2,4-dichlorophenoxyacetic acid), picloram and IBA, and then collecting the cambium-derived cells.

5. A method of ameliorating AIDS, the method comprising orally administering functional food comprising a cell line derived from the cambium of *Panax ginseng*, wherein the cell line has the following characteristics:
   (a) it is in an innately undifferentiated state; and
   (b) it is a homogeneous cell line.

6. The method of claim 5, wherein the cell line further has the following characteristics:
   (a) it is present as single cell level during a suspension culture;
   (b) it has a lower sensitivity to shear stress in a bioreactor, compared to cell lines derived from tissues other than the cambium of *Panax ginseng*; and
   (c) its growth rate is higher than those of cell lines derived from tissues other than the cambium of *Panax ginseng* and is cultured stably.

7. The method of claim 5, wherein the cell line is obtained by using an isolation method comprising the steps of:
   (a) obtaining a *Panax ginseng* cambium-containing tissue;
   (b) culturing the cambium-containing tissue in a medium supplemented with IAA or IBA to induce a cell line derived from the cambium, wherein an osmotic stress is applied to the cambium-containing tissue before, during, or after the culture; and
   (c) collecting the induced, cambium-derived cell line.

8. The method of claim 7, wherein step (c) is performed by proliferating the induced cambium-derived cell line in a medium which contains one or more of 2,4-D (2,4-dichlorophenoxyacetic acid), picloram and IBA, and then collecting the cambium-derived cells.

9. A method of increasing T cells, the method comprising administering a cell line, derived from the cambium of *Panax ginseng*, wherein the cell line and has the following characteristics:
   (a) it is in an innately undifferentiated state; and
   (b) it is a homogeneous cell line.

10. The method of claim 9, wherein the cell line is obtained by using an isolation method comprising the steps of:
    (a) obtaining a *Panax ginseng* cambium-containing tissue;
    (b) culturing the cambium-containing tissue in a medium supplemented with IAA or IBA to induce a cell line derived from the cambium, wherein an osmotic stress is applied to the cambium-containing tissue before, during, or after the culture; and
    (c) collecting the induced, cambium-derived cell line.

11. The method of claim 10, wherein step (c) is performed by proliferating the induced cambium-derived cell line in a medium which contains one or more of 2,4-D (2,4-dichlorophenoxyacetic acid), picloram and IBA, and then collecting the cambium-derived cells.

* * * * *